United States Patent
Chen

(10) Patent No.: US 10,238,717 B2
(45) Date of Patent: Mar. 26, 2019

(54) PARENTERAL GLUCAGON FORMULATIONS

(71) Applicant: Latitude Pharmaceuticals, Inc., San Diego, CA (US)

(72) Inventor: Andrew Chen, San Diego, CA (US)

(73) Assignee: LATITUDE PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/475,032

(22) Filed: Mar. 30, 2017

(65) Prior Publication Data

US 2017/0202926 A1    Jul. 20, 2017

Related U.S. Application Data

(63) Continuation of application No. PCT/US2015/057152, filed on Oct. 23, 2015.

(60) Provisional application No. 62/069,097, filed on Oct. 27, 2014.

(51) Int. Cl.
| | |
|---|---|
| *A61K 47/10* | (2017.01) |
| *A61K 38/26* | (2006.01) |
| *C07K 14/605* | (2006.01) |
| *A61K 9/00* | (2006.01) |
| *A61K 9/08* | (2006.01) |
| *A61K 47/02* | (2006.01) |
| *A61K 47/18* | (2017.01) |
| *A61K 47/26* | (2006.01) |

(52) U.S. Cl.
CPC ............ *A61K 38/26* (2013.01); *A61K 9/0019* (2013.01); *A61K 9/08* (2013.01); *A61K 47/02* (2013.01); *A61K 47/10* (2013.01); *A61K 47/183* (2013.01); *A61K 47/26* (2013.01); *C07K 14/605* (2013.01)

(58) Field of Classification Search
None
See application file for complete search history.

(56) References Cited

U.S. PATENT DOCUMENTS

| | | |
|---|---|---|
| 6,270,700 B1 | 8/2001 | Ignatious et al. |
| 6,417,237 B1 | 7/2002 | Dadey et al. |
| 2002/0107265 A1 | 8/2002 | Chen et al. |
| 2006/0067952 A1 | 3/2006 | Chen |
| 2008/0318865 A1 | 12/2008 | Juul-Mortensen et al. |
| 2011/0091420 A1 | 4/2011 | Liu et al. |
| 2011/0097386 A1 | 4/2011 | Steiner et al. |
| 2011/0237510 A1* | 9/2011 | Steiner .................. A61K 9/0019 514/11.7 |
| 2012/0046225 A1* | 2/2012 | Prestrelski ........... A61K 9/0019 514/6.8 |
| 2014/0221288 A1 | 8/2014 | Prestrelski et al. |
| 2014/0287998 A1 | 9/2014 | Rylander et al. |
| 2014/0378381 A1 | 12/2014 | Chen et al. |

FOREIGN PATENT DOCUMENTS

| | | |
|---|---|---|
| JP | 2002521343 | 7/2002 |
| KR | 10-2007-0063023 | 6/2007 |
| WO | 2009121069 | 10/2009 |
| WO | 2013101749 | 7/2013 |

OTHER PUBLICATIONS glucagon, the package insert for Eli Lilly's glucagon formulation (revised 2005).*
The DFE pharma pamphlet on lactose, published Oct. 2013.*
Van Arnum, Patricia, "Antinnirobial preservatives in protein drugs." Pharmtech.com, publication of Nov. 3, 2006.*
Chen et al., "Nanonization strategies for poorly water-soluble drugs", Drug Discovery Today, vol. 16, No. 7, Apr. 2011, pp. 354-360.
Devarajan et al., "Nanoemulsions: As Modified Drug Delivery Tool", Pharmacie Globale: International Journal of Comprehensive Pharmacy (IJCP), Pharmacie Globale, India, vol. 4, No. 2, Apr. 5, 2011, pp. 1-6.
Gutierrez et al., "Nano-emulsions: New applications and optimization of their preparation", Curren Opinion Colloid and Interface Science, London, GB, vol. 13, No. 4, Aug. 1, 2008, pp. 245-251.
Onoue et al., "Inhalable sustained-release formulation of glucagon: in vitro amyloidogenic and inhalation properties, and in vivo absorption and bioactivity", Pharmaceutical Research, Kluwer Academic Publishers-Plenum Publishers, NL, vol. 28, No. 5, Feb. 2, 2011, pp. 1157-1166.
International Search Report and Written Opinion dated Jan. 19, 2016 for PCT/US2015/057152, 7 pages.

* cited by examiner

*Primary Examiner* — Fred H Reynolds
(74) *Attorney, Agent, or Firm* — Kilpatrick Townsend & Stockton LLP

(57) ABSTRACT

This invention relates to compositions of glucagon suitable for administration by manual injection or by an insulin pump or other injection device to treat hypoglycemia. Said compositions comprise glucagon and a sugar, have a final pH between about 1.5 and 3, and are gel-free, chemically-stable at body temperature and pump-able.

21 Claims, No Drawings

PARENTERAL GLUCAGON FORMULATIONS

CROSS-REFERENCE TO RELATED APPLICATIONS

The present application is a Continuation of PCT/US2015/057152 filed Oct. 23, 2015; which claims priority to U.S. Provisional Application No. 62/069,097 filed Oct. 27, 2014; the full disclosures of which are incorporated herein by reference in their entirety for all purposes.

FIELD OF THE INVENTION

This invention relates to injectable liquid compositions comprising glucagon and sugar, which are useful for the treatment and prevention of hypoglycemia.

BACKGROUND OF THE INVENTION

Glucagon, a hormone secreted by the pancreas, is a polypeptide consisting of a single chain of 29 amino acids with a molecular weight of 3,485 Da. Glucagon stimulates the liver to convert stored glycogen into glucose, which is released into the blood. Medically, glucagon is used primarily to treat hypoglycemia (a condition of lower than normal blood glucose concentrations) due to insulin overdose. Glucagon is also used during radiologic examinations of the stomach, duodenum, small bowel, and colon when diminished intestinal motility is required. For pharmaceutical use, glucagon can be made by chemical synthesis, recombinant DNA technology or derived from an animal source.

The two currently marketed glucagon drug products, GlucaGen® Hypokit (glucagon hydrochloride) from Novo Nordisk A/S and Glucagon for Injection (rDNA Origin) from Eli Lilly and Company ("Glucagon Emergency Kit for Low Blood Sugar") are provided as two-part kits. The GlucaGen® Hypokit consists of a vial containing 1 mg glucagon as hydrochloride and 107 mg lactose monohydrate in a lyophilized solid ("lyo cake") and a disposable syringe that contains sterile water for reconstituting the lyo cake. The lyo cake provides a dry environment that keeps glucagon chemically stable. The reconstituted solution contains glucagon as hydrochloride 1 mg/mL (1 unit/mL) and lactose monohydrate (107 mg) at pH 2.5-3.5. The Glucagon Emergency Kit for Low Blood Sugar contains a vial of sterile lyophilized glucagon and a syringe of sterile diluent. The lyo cake contains 1 mg (1 unit) of glucagon and 49 mg of lactose. The diluent syringe contains 12 mg/mL of glycerin, Water For Injection, and hydrochloric acid. The reconstituted solution contains glucagon 1 mg/mL (1 unit/mL) glucagon and 49 mg/mL lactose at pH 2.0-3.5. To use the Kit, the diluent is first injected into vial with the lyo cake to dissolve it. The reconstituted glucagon solution obtained is then drawn back into a syringe and then injected. The reconstituted glucagon solutions for both the GlucaGen® Hypokit and the Glucagon Emergency Kit for Low Blood Sugar thus obtained are chemically and physically unstable and therefore must be used immediately. The glucagon used in both kits is produced by DNA recombinant technology.

Insulin pumps have been widely used by type-1 diabetics for over a decade. An insulin pump can be worn by a patient externally in close proximity to the body and delivers insulin via fine tubing through subcutaneously implanted needles. The subcutaneous needles may remain in place for up to a week. Continuous glucose monitoring sensors or "CGM" capable of continuously reading blood glucose levels can be used to provide blood glucose level information to the insulin pump to control insulin output in real time. However, when too much insulin has been pump-delivered, the current versions of the insulin pump do not have an effective means to counteract the drop in blood glucose and impending hypoglycemia from the already-administered insulin. In the normal individual, the pancreas naturally counteracts rapid blood glucose decreases by secreting glucagon, but in a Type-1 diabetic patient, such function is impaired due to the diminished alpha cell activity.

A "bi-hormonal artificial pancreas" consisting of a CGM-controlled bi-hormonal pump that delivers both insulin and glucagon, has the potential to closely control blood glucose levels. When blood glucose reaches or is anticipated to reach hypoglycemic levels, the bi-hormonal pump could deliver glucagon to counteract instances of insulin-induced hypoglycemia. This dual drug capability will allow better blood glucose regulation similar to that achieved by the insulin/glucagon system of the normal pancreas.

A bi-hormonal pump requires a liquid glucagon formulation that is chemically and physically stable for at least 3.5 to 7 days at or near body temperature. Currently, insulin pump users replenish insulin approximately every half week. Therefore, 3.5-7 days was selected as a convenient replenishment cycle. Furthermore, the glucagon formulation must be "pump-able", i.e., it can be delivered accurately and reliably in small volumes (e.g., 10-50 microliters) by a pump through narrow-bore infusion tubing. To be pump-able, the glucagon formulation must also have an acceptable viscosity and be chemically compatible with the pump and infusion set. For this reason, strong solvents such as DMSO are not desired.

Glucagon has an isoelectric point of 7.1 and is thus insoluble in water at physiological pH (pH 4-8). At pH 3 or lower, it is initially soluble, but within hours, it will aggregate to form a gel. The gelled glucagon consists predominantly of β-sheets or fibrils (Chou, P. Y., et al. 1975. Biochemistry 14(11):2536-2541) and can clog up the narrow tubing of the infusion set. Therefore, gelled or aggregated glucagon preparations are thus not pump-able. The glucagon fibrils or gels are also unsafe for injection.

In addition to forming gels, glucagon undergoes various types of chemical degradation. In solution, glucagon rapidly degrades chemically to form numerous degradation products. At least 16 degradation products of glucagon have been identified with the major degradation pathways being aspartic acid cleavage at positions 9, 15, and 21 and glutaminyl deamidation at positions 3, 20 and 24 (Kirsch, L. E., et al. 2000. International Journal of Pharmaceutics, 203:115-125). The chemical degradation of glucagon is rapid and complex. For example, a glucagon solution prepared from the GlucaGen® Hypokit loses about 60-70% of glucagon within 7 days at 37° C. (see Example 2). Therefore, the current commercial glucagon kits are not suitable for a bi-hormonal pump use.

Preventing glucagon degradation in aqueous solutions is very difficult and no effective method has been reported to effectively inhibit glucagon gelling and degradation.

WO 2013086292 A1 discloses glucagon formulations comprising glucagon, a bulking agent, and an acidifying agent in a pharmaceutically acceptable diluent. The composition can be readily lyophilized and rapidly reconstituted with its diluent. The bulking agents may include carbohydrates, amino acids, salts, mannitol, lactose, sucrose, dextran, sodium chloride, and combinations thereof. A bulking agent or matrix builder must provide a solid structure (i.e., a "cake") or a powder after lyophilization. The disclosed formulation used mannitol as a bulking agent at concentrations from approximately 1.0% to approximately 10.0% (w/v).

WO2012059764 teaches aqueous compositions having a pH between 4 and 7 comprising glucagon and a cationic surfactant as solubilising agent. Examples of cationic surfactants include benzethonium salts, benzalkonium salts, and cetyl trimethylammonium salts. Cationic surfactants are toxic and not desirable for the long-term chronic use contemplated for the bi-hormonal pump.

WO 2011049713 claims a formulation comprising a sugar and a surfactant, wherein "sugar" refers to a monosaccharide or disaccharide with preferred examples including sucrose, maltose and glucose in a concentration range of about 20-100 mg/mL, preferably 0.25 M (which is equivalent to 8.6% w/v, 8.6% w/v and 4.5% w/v, respectively, for sucrose, maltose and glucose).

US20120232001 claims a stable formulation comprising: (a) a peptide or a salt thereof, wherein the peptide has been dried in a non-volatile buffer, and wherein the dried peptide has a pH memory that is about equal to the pH of the peptide in the non-volatile buffer; and (b) an aprotic polar solvent wherein the moisture content of the formulation is less than 5%, and wherein the dried peptide maintains the pH memory that is about equal to the pH of the peptide in the non-volatile buffer when the dried peptide is reconstituted in the aprotic polar solvent. Examples of aprotic polar solvents include dimethylsulfoxide (DMSO), dimethylformamide (DMF), ethyl acetate, n-methyl pyrrolidone (NMP), dimethylacetamide (DMA), and propylene carbonate. Formulations described therein are essentially non-aqueous. The safety of the aprotic polar solvents for the chronic use contemplated for the bi-hormonal pump is questionable.

WO1995032730 discloses a pharmaceutical preparation comprising glucagon and a stabilizing amount of a pharmaceutically acceptable ampholyte except histidine.

None of the above disclosed compositions can meet all of the following requirements desired for a new glucagon formulation:
1. Comprises an aqueous solution
2. Stable (i.e., non-gelling and chemically stable) for 3.5 to 7 days at 37° C.
3. Pump-able.

There still is a need for pharmaceutical formulations of glucagon that overcome the limitations of the above described approaches.

SUMMARY OF THE INVENTION

In an aspect, this invention provides a stable glucagon formulation that is an aqueous, stable and pump-able solution.

In another aspect, this invention provides a glucagon formulation that is suitable for injection or delivery by an insulin pump or bi-hormonal pump or glucagon pump.

In yet another aspect, this invention provides a glucagon formulation comprising glucagon and a sugar.

This invention also provides a method to make a stable glucagon formulation comprising glucagon and a sugar.

In yet another aspect, this invention provides a method for treatment or prophylaxis for a patient by directly injecting a hypertonic sugar solution into a soft tissue of the patient.

This invention also provides a method of using a stable glucagon formulation comprising glucagon and a sugar to prevent or reduce and treat hypoglycemia by injecting the formulation with a syringe, an insulin pump, a bi-hormonal pump or a glucagon pump.

These and other aspects, which will become apparent during the following description, have been achieved by the inventor's discovery that a sugar at certain high concentrations can be useful for stabilizing glucagon.

DETAILED DESCRIPTION OF THE INVENTION

I. Definitions

The various terms used herein shall have the following definitions:

As used herein, "about" describes a quantity with a range covering 10% expansion from both sides of the target value. For example, "about 100" means any value between 90 and 110 including 90 and 110.

As used herein, an "acid" refers to any organic or inorganic acid that is suitable for injection or an injectable acid. The injectable acids are acids that have previously approved by the FDA for use in injectable drugs and are identified on the FDA's Inactive Ingredient List. Acids that are particularly useful for this invention include, but are not limited to, acetic acid, ascorbic acid, aspartic acid, benzenesulfonic, benzoic acid, citric acid, formic acid, fumaric acid, hydrochloric acid, hydrobromic acid, lactic acid, lactobionic acid, maleic acid, malic acid, malonic acid, methanesulfonic acid, phosphoric acid, propionic acid, succinic acid, sulfuric acid, and tartaric acid. The preferred acids are those having a pKa less than 5. The more preferred acids are citric acid, hydrochloric acid, lactic acid, methanesulfonic acid, phosphoric acid, propionic acid, sulfuric acid, and tartaric acid.

As used herein, the phrase "anti-gelling" refers to the ability of certain agents to prevent glucagon gelation, aggregation or fibril-formation.

An "antioxidant" is a pharmaceutical additive that can be added to a liquid composition to prevent oxidation of the active drug or an inactive component. Antioxidants include, but are not limited to, reducing agents, metal ion chelating agents and inert gases.

As used herein, "aqueous" means that the composition is made with water as a liquid vehicle and is substantially free of an organic solvent.

As used herein, "body temperature" is about 37° C. and "near body temperature" is about 30 to 40° C.

As used herein, "chemically-stable" means the composition retains no less than 80% of the initial glucagon concentration after 3.5 to 7 days exposure to the body temperature and certain agitation. Storage for 7 days at the body temperature with certain agitation is the normal use condition for a glucagon composition to be used in an insulin pump or bi-hormonal pump.

As used herein, "Commercially Available Injectable Drugs/Preparations" refers to an FDA approved, commercially available drug product for injection or diluents for injection. These products are manufactured using an FDA-approved process (e.g., GMP) and meeting FDA-accepted quality specifications (e.g., USP). These products may be purchased with or without prescriptions. Examples of Commercially Available Injectable Drugs/Preparations may include, but are not limited to, the GlucaGen® Hypokit, 50% Dextrose for Injection, USP, 70% Dextrose Injection, USP, 20% Mannitol Injection, USP, Edetate Disodium Injection, USP, Edetate Calcium Disodium Injection, USP, Bacteriostatic Water for Injection, USP As used herein, "FDA" refers to the US Food and Drug Administration.

As used herein, "filterable" means the ability of a liquid to pass through a filter membrane of a certain pore size such as 0.2 microns. The glucagon solution compositions of the present invention are filterable when they are prepared.

As used herein, "glucagon" refers to the full length peptide, glucagon, having the empirical formula of $C_{153}H_{225}N_{43}O_{49}S$, a molecular weight of 3,483 Da., CAS #16941-32-5, and composed of a single-chain polypeptide containing 29 amino acid residues, with the following amino acid sequence: NH$_2$-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-COOH, or any other peptide protein or chemical drug that contains a glucagon-like sequence or shares the same aggregation, gelling or chemical degradation problems as glucagon.

As used herein, "glucagon fibril" means aggregated glucagon that presents in particles or fiber-like structures. Glucagon fibrils can be detected visually or quantitated by certain analytical methods such as particle size analysis as described in USP <788>. Extensive formation of glucagon fibrils in a glucagon composition will cause it to fail the USP <788> test specification, rendering the composition unsafe for injection into a patient.

As used herein, the term "hypertonic" means a solution having an osmotic pressure (whether measured or calculated) exceeding 600 mOsmol/L. The glucagon solution compositions of the present invention are hypertonic.

As used herein, an "insulin pump" is a medical device used for the administration of insulin in the treatment of diabetes mellitus, such as in subcutaneous continuous insulin infusion therapy. The device includes a pump (having controls, a processing module, and batteries), a disposable reservoir for insulin (inside the pump), a disposable infusion set consisting of a tubing system to connect the pump reservoir with a cannula for subcutaneous delivery of insulin. An insulin pump may also deliver a second solution such as a glucagon solution to prevent or treat insulin overdose or hypoglycemia. An insulin pump capable of delivering two solutions is also referred to as a bi-hormonal pump. As used herein, the term "insulin pump" may be used interchangeably with "bi-hormonal pump" or "subcutaneous infusion pump".

As used herein, an "intravascular injection" refers to an injection or administered by entry directly into a blood vessel such as an intravenous or intra-arterial injection. A non-intravascular injection refers to an injection or administered by entry directly into a soft tissue. Non-intravascular injections may include subcutaneous, intramuscular, intradermal, and intracavernous injections.

The term "metal ion chelating agent or chelator" includes metal ion chelators that are safe to use in an injectable product. A metal ion chelator works by binding to a metal ion and thereby reduces the catalytic effect of that metal ion on the oxidation, hydrolysis or other degradation reactions. Metal chelators that are useful in this invention may include ethylenediaminetetraacetic acid (EDTA, edetate), glycine and citric acid and the respective salts or a mixture thereof. Examples of the preferred chelators include sodium, potassium or calcium salts of EDTA.

As used herein, the phrase "non-gelling" means a glucagon composition that exhibits no visible glucagon precipitates, particles, fibrils or gels AND it passes the USP test specification for "PARTICULATE MATTER IN INJECTIONS" as described in USP monograph <788>. Specifically, "non-gelling" means a glucagon composition that, after 3.5 to 7 days storage at body temperature, meets the following requirements:

| | Particle | |
|---|---|---|
| | ≥10 µm Particle | ≥25 µm Particle |
| USP <788> specification | No more than 6000 per container | No more than 600 per container |

Meeting the USP <788> specification is generally required for all injectable solution formulations, including any injectable glucagon formulation, in order to be considered safe for human use.

As used herein, the term "parenteral" means a route of administration of a drug/preparation by some means other than oral or rectal intake, particularly intravenously or by injection.

As used herein, "pH" is a measure of the acidity or basicity of an aqueous solution. The pH determination of a composition of the present invention is typically performed with a pH meter consisting of a glass electrode connected to an electronic meter that measures and displays the pH. The pH meter is calibrated using aqueous standard pH buffers. Solutions with a pH less than 7 are said to be acidic and solutions with a pH greater than 7 are basic or alkaline. Pure water has a pH very close to 7.

As used herein, "preservative" is a pharmaceutical additive that can be added to a liquid composition to inhibit the growth of bacteria and fungi. The antimicrobial preservatives useful in the present invention include, but are not limited to, cresols, phenol, benzyl alcohol, ethanol, chlorobutanol, parabens, imidura, benzylkonium chloride, EDTA or its salt or a combination thereof.

As used herein, the phrase "pump-able" means that a solution can be delivered by an insulin pump or bi-hormonal pump with delivery volume accuracy within 80 to 120% and that the solution is of sufficiently low viscosity to allow the infusion tubing to be primed with solution delivered from an insulin or bi-hormonal pump.

As used herein, the term "reconstitution" refers to the process of returning a dehydrated, concentrated or lyophilized state to the liquid state by adding water or other liquid diluent.

As used herein, the term "saturation" means that a solute has reached its maximum solubility in a solvent. For example, at saturation, the concentration of a sugar in water is about 90.9% w/v for dextrose (25° C.), about 21.6% w/v for lactose (25° C.), about 200% w/v for sucrose (25° C.), about 68.9% w/v for trehalose (20° C.), about 25% w/v for mannitol, and about 22% w/v for sorbitol (20° C.). The saturation level for a sugar in water can be found in literature or determined experimentally. In general, a sugar useful for the present invention has a saturation level in water greater than 20% w/v, and the concentration of a sugar useful for the present invention is greater than 20% w/v and up to the saturation of the sugar.

As used herein, the term "substantially free" means less than 1% of the total composition weight.

As used herein, a "sugar" refers to water-soluble mono-, di-, oligo- and polysaccharides that are suitable for injection or are injectable. Some sugars that have previously been approved by the FDA for use in injectable drugs and are identified on the FDA's Inactive Ingredient List. Sugars that are useful for this invention include, but are not limited to, dextrose, glucose, invert sugar, trehalose, galactose, fructose, ribose, deoxyribose, ribulose, xylulose, xylose, mannose, lactose, sucrose, maltose, fructo-oligosaccharides (FOS), galacto-oligosaccharides (GOS), mannan oligosaccharides (MOS), amylose, amylopectin, starch and glycogen. A sugar may also refer to one of the sugar alcohols, which includes glycerol, mannitol, maltitol, sorbitol, xylitol, erythritol, and isomalt. The preferred sugars for this invention are dextrose, glucose, lactose, sucrose, mannitol and sorbitol. A sugar may also refer to a combination of 2 or more sugars. The preferred sugar combinations for this invention are a combination of lactose and dextrose, a combination of lactose and mannitol, and a combination of lactose and sucrose.

Normally, sugars are used in an injectable composition to adjust osmotic pressure or tonicity to be equivalent to the normal saline ("isotonic") and to protect the composition during freezing, thawing or lyophilization (as a "cryoprotectant"). The sugar concentration used in the current glucagon composition (20% or more) is much higher than what is normally used to achieve isotonicity or for cryoprotection. For example, the typical concentration used to make a solution isotonic is about 2.1% for glycerol, 5% for mannitol or lactose, 8.5% for sucrose or trehalose and the typical concentration used for a cryoprotection is about 5-10% for mannitol, lactose or sucrose. When the sugar concentration exceeds 10%, the solution becomes hypertonic and is generally contraindicated for subcutaneous or intramuscular injection because hypertonic solutions are assumed to produce pain and irritation at the injection site.

As used herein, "solution" refers to a clear, homogeneous liquid mixture composed of only one phase.

As used herein, "USP" means the current edition of the United States Pharmacopeia.

As used herein, the term "%" means the weight by volume percentage, or % w/v. For example, 1% means one gram in 100 mL or 10 mg/mL.

As used herein, the term "% w/w" means the weight by weight percentage, or % w/w. For example, 1% w/w means one gram in 100 g or 10 mg/g.

In general, a high-concentration sugar solution of the current invention has a density or specific gravity of about 1.1 to 1.3 g/mL at room temperature. Therefore the weight by volume percentage concentration may be converted to weight by weight percentage as follows: % w/v=% w/w× density value. For example, density of a 50% w/w dextrose solution at 20° C. is 1.223 g/mL. The weight by volume percentage concentration of this solution is therefore 50% w/w×1.223 g/mL=61.15% w/v.

II. Description

A bi-hormonal pump that delivers both insulin and glucagon to maintain euglycemia, the output of which is controlled by CGM-determined blood glucose levels, would be highly desired by insulin-using diabetics. For pump users, it would be desirable to replenish the disposable insulin and glucagon pump reservoirs and the disposable infusion set on a once-a-week or twice-a-week basis. As the pump is in close proximity to the patient's body, it is important for the insulin and glucagon solutions to remain stable and pumpable for 3.5 to 7 days at body temperature in the presence of agitation that represents normal ambulatory activity. The currently marketed glucagon products (GlucaGen® Hypokit (Novo Nordisk A/S) and Glucagon Emergency Kit for Low Blood Sugar (Eli Lilly and Co.)) are not suitable for such pump use because in these formulations, the glucagon rapidly degrades and forms fibrils in just a few hours after reconstitution with the provided solutions.

In a search for a more stable glucagon composition, this inventor made the unexpected discovery that high concentration sugar solutions (i.e., greater than 20% and up to saturation concentrations) surprisingly could stabilize glucagon in aqueous solutions by preventing or inhibiting fibril formation and chemical degradation, thereby providing a stable and pump-able aqueous glucagon solution.

The concentrations of sugar utilized in present invention are much higher than what is normally used for isotonicity or cryoprotection. For example, about 4-5% for a monosaccharide and 8-10% for a di-saccharide is required to achieve an isotonic osmolarity of about 290-300 mOsmol/L. For cryoprotection, the typical sugar concentration used is 2-10% w/v, which covers the lactose concentration in the GlucaGen® Hypokit (about 10%) and in the Glucagon Emergency Kit for Low Blood Sugar (about 4.9%).

A concentrated sugar solution (i.e., greater than isotonic) or a hypertonic sugar solution is contraindicated for direct injection (undiluted) into soft tissue because of concern for possible pain and injection site irritation. Indeed, the Prescribing Information for commercially available 50% and 70% Dextrose Injection, USP contains a precaution that these solutions should not be administered subcutaneously or intramuscularly. The same Prescribing Information notes that such high concentration sugar solutions should be injected slowly into the vein to minimize irritation.

This inventor discovered that, surprisingly, a hypertonic sugar solution (50% dextrose solution having an osmotic pressure as high as about 2,523 mOsmol/L) is non-irritating and did not produce any noticeable pain when injected subcutaneously from an insulin pump. This discovery was unexpected because it is in contrast to both what has been taught in the prior art and what is the current medical practice. This finding provides the safety rationale to support non-intravascular soft tissue administration of hypertonic sugar solutions, such as the glucagon composition of the present invention.

This inventor also made the unexpected discovery that the presence of sugars at concentrations of 20% or more in glucagon solutions could inhibit the chemical degradation of glucagon, most noticeably the deamidation reactions. This can result in significantly better glucagon stability in aqueous solutions containing greater than 20% sugar than in solutions containing lesser amounts. For example, after 7 days incubation at 37° C., the intact glucagon recovered from a 10% sugar solution was about 37.6% but was much higher (79.6%) in a 50% sugar solution. (Example 2).

In addition, this inventor discovered, surprisingly, that glucagon fibrillation, aggregation or gelation could be inhibited in glucagon solutions containing sugar at 20% or higher. For example, the glucagon solution prepared by mixing the diluent and lyo cake in the GlucaGen® Hypokit contains about 10% lactose and consistently forms a gel within 7 days when incubated at 37° C. By adding additional sugar from prepared sugar solutions (e.g., 10 to 70% dextrose, 10 to 25% mannitol, 10% lactose, or 10 to 40% sucrose) to bring the final sugar concentration to 20% or greater could effectively reduce glucagon fibril, aggregation or gels formation. This enhanced stability could thus keep glucagon solutions pump-able under the same use conditions.

Thus, in an aspect, the present invention provides a parenteral formulation, comprising:
 a. Glucagon
 b. About 20 to 90% sugar; and
 c. About 10 to 80% water.

In one aspect, each milliliter of the composition of this invention contains 0.5 to 3 mg of glucagon. In a more preferred aspect, each milliliter of the composition of this invention contains about 1 mg of glucagon. In yet another preferred aspect, each milliliter of the composition of this invention contains 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 mg of glucagon.

In another aspect, the present invention provides a parenteral formulation, wherein the pH is from 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.5, 5, 5.5, 6.0, 6.5, 7.0, 7.5, 8.0, 8.5, 9.0, 9.5 to 10. Additional examples of the pH include (a) 2.2, (b) 2.5, (c) 2.7, (d) 3.0, (e) 3.3, (f) 2.0-3.0, and (g) 2.5-3.5.

In yet another aspect, the present invention provides a parenteral formulation, comprising an acid. The acid selection is dependent upon the glucagon fibrillation and chemical stability in the formulation. The acid can be selected based on its inhibitory effect on glucagon fibrillation and/or degradation. The amount of acid to use is determined by the final pH desired which is in the range from 0.01 to 1M. The preferred acid is citric acid, hydrochloric acid, lactic acid, methanesulfonic acid, phosphoric acid, propionic acid, sulfuric acid, tartaric acid or a mixture thereof. The most preferred acid is hydrochloric acid.

In yet another aspect, the present invention provides a parenteral formulation, comprising a preservative. For use in an insulin or bi-hormonal pump, a liquid formulation of glucagon is desired to have a preservative due to the repeated and prolonged dosing, which increases risk of microbial contamination. Thus, a preservative which inhibits such microbial activities is useful for the inventive glucagon composition. The type of preservative to use can be selected based on its antimicrobial efficacy and safety to the patients. In general, preservatives that have previously been approved by the FDA for subcutaneously injectable drugs are considered suitable for use for present invention. The quantity of each preservative to use can be determined based on certain accepted standards (e.g., Antimicrobial Effectiveness Testing USP <51>)). The preferred preservative for the present invention is cresol, metacresol (m-cresol), phenol, parabens, benzyl alcohol, EDTA or a mixture thereof. The concentrations may be used are about 0.08 to 0.315% for cresol/metacresol, 0.06 to 1.3% for phenol, 0.01 to 1.5% for a paraben, 0.05 to 10% for benzyl alcohol, 0.005 to 0.2% for EDTA disodium, and 0.005 to 0.34% for EDTA calcium disodium.

In an aspect, the present invention provides a parenteral formulation, comprising:
 a. About 0.1 to 10 mg/mL glucagon
 b. About 20, 30, 40, 50, 60, 70, or 80 to 90% w/v sugar; and
 c. About 10, 20, 30, 40, 50, 60, or 70 to 80% w/v water.

In an aspect, the present invention provides a parenteral formulation, comprising:
 d. About 0.1 to 10 mg/mL glucagon
 e. About 20, 30, 40, 50, 60, 70, or 80 to 90% w/v dextrose; and
 f. About 10, 20, 30, 40, 50, 60, or 70 to 80% w/v water.

In yet another aspect, the present invention provides a parenteral formulation, comprising:
 a. About 0.1 to 10 mg/mL glucagon
 b. About 4.9 to 10% w/v lactose
 c. About 10, 20, 30, 40, 50, 60, 70, or 80 to 90% w/v dextrose; and
 d. About 10, 20, 30, 40, 50, 60, or 70 to 80% w/v water.

In another aspect, the present invention provides a parenteral formulation, comprising:
 a. About 0.05 to 5 mg/mL glucagon
 b. About 4.9 to 10% w/v lactose
 c. About 50 to 70% w/v dextrose; and
 d. About 20, 30, or 40 to 45% w/v water.

In another aspect, the formulation of the present invention has a pH from 2.0 to 3.

In another aspect, the formulation of the present invention has a viscosity at between about 10 and 50,000 mPas.

In another aspect, the formulation of the present invention is self-preserving because the high concentration of sugar prevents microbial growth in the formulation.

In another aspect, the formulation contains a preservative at a concentration that enables the formulation to pass the USP specification of Antimicrobial Effectiveness Testing (i.e., USP <51>).

In another aspect, the present invention provide a parenteral formulation, comprising:
 a. About 1 mg/mL glucagon
 b. About 4.9% w/v lactose
 c. About 40 to 70% w/v dextrose
 d. About 0.1 to 0.3% w/v metacresol, and
 e. Sufficient amount of hydrochloride acid to adjust pH to 2.0 to 3.

In another aspect, the present invention provide a parenteral formulation, comprising:
 a. About 1 mg/mL glucagon
 b. About 10% w/v lactose
 c. About 40 to 70% w/v dextrose
 d. About 0.1 to 0.3% w/v metacresol, and
 e. Sufficient amount of hydrochloride acid to adjust pH to 2.5 to 3.5.

In one aspect, the composition of this invention further contains an antioxidant. The useful antioxidants may include but not limited to an inert gas, methionine, cysteine, dextrose, fructose, lactose, and a salt of edetate (EDTA), or combination thereof. A preferred antioxidant is a combination of methionine and EDTA. The concentration of each antioxidant may be determined based on its stabilizing effect on glucagon in the composition of this invention and its safety to the patient. A normal range of concentration for each antioxidant for subcutaneous injection can be found in the FDA's Inactive Ingredient List. For example, the methionine concentration range useful for injectable formulations is 0.01% to 49.2%.

In another aspect, the present invention provides a method to prepare a parenteral formulation, comprising: (1) combining glucagon, a sugar; and water to form an aqueous solution, and (2) adjusting pH to the desired value using an acid.

In another aspect, the present invention provides a method to prepare a parenteral formulation, comprising: (1) adding a solution containing about at least 20% w/v a sugar to a lyophilized solid composition comprising glucagon, and (2) mixing to obtain an aqueous solution.

In another aspect, the present invention provides a method to prepare a parenteral formulation, comprising the addition of water to a lyophilized solid composition comprising glucagon and sugar. The said lyophilized solid composition contains the calculated amounts of glucagon and sugar such that upon reconstitution with water, it forms an aqueous solution of the inventive composition.

In another aspect, the present invention provides a method to prepare a parenteral formulation, comprising: (1) adding a 50% or 70% w/v dextrose solution, USP to the vial containing a lyophilized glucagon "lyo cake" (the same as or similar to what is provided in the GlucaGen® Hypokit or the Glucagon Emergency Kit for Low Blood Sugar), and (2) mixing to obtain a clear solution. Each lyo cake comprises glucagon and lactose.

In another aspect, the present invention provides a method to prepare a parenteral formulation, comprising mixing two or more Commercially Available Injectable Drugs/Preparations including one containing glucagon and one containing a sugar in such a mixing ratio that the final mixture is a clear solution containing the glucagon composition of the present invention. In addition, another Commercially Available Injectable Drug/Preparation containing a preservative or antioxidant may be added to the mixture. For example, the following Commercial Available Injectable Drugs/Preparations may be mixed conveniently to prepare a glucagon composition of the present invention:

| Commercially available injectable drugs/preparations | Composition of commercially available injectable drugs/preparations | Used as a source for |
| --- | --- | --- |
| GlucaGen® Hypokit from Novo Nordisk | Each vial contains 1 mg glucagon, 107 mg lactose monohydrate and hydrochloric acid in a lyophilized cake. pH (after dissolving in 1 mL water) is 2.0-3.5 | Glucagon (vial with the lyo cake only) |
| Glucagon for Injection (rDNA Origin) from Eli Lilly and Company, (Glucagon Emergency Kit for Low Blood Sugar) | Each vial contains a 1 mg glucagon and 49 mg lactose and hydrochloric acid in a lyophilized cake. pH (after dissolving in 1 mL water) is 2.0-3.5 | Glucagon (vial with the lyo cake only) |
| 50% Dextrose Injection, USP ("D50W") | Each mL contains 500 mg dextrose, pH is about 4 | Sugar (diluent) |
| 70% Dextrose Injection, USP ("D70W") | Each mL contains 700 mg dextrose, pH is about 4 | Sugar (diluent) |
| 20% Mannitol Injection, USP | Each mL contains 200 mg mannitol in water. pH is about 5.3 (4.5-7.0) | Sugar (diluent) |
| Edetate Disodium Injection, USP | Each mL contains edetate disodium, anhydrous 150 mg in water. pH is about 7 (6.5 to 7.5) | Preservative or antioxidant |
| Edetate Calcium Disodium Injection, USP | Each mL contains 200 mg of edetate calcium disodium in water. pH is about 7 (6.5 to 8.0) | Preservative or antioxidant |
| Bacteriostatic Water for Injection, USP | Each mL contains 9 mg benzyl alcohol in water. pH is about 5.7 (4.5 to 7.0) | Preservative |

In one aspect, the present invention provides a method to prepare a parenteral formulation, comprising adding about 1 mL 50% Dextrose Injection, USP to the glucagon vial provided in the GlucaGen® Hypokit, mixing to obtain a clear solution composition of the present invention which contains about 1 mg/mL glucagon, about 10% lactose, and about 50% dextrose at a pH of about 2.0 to 3.5.

In one aspect, the present invention provides a method to prepare a parenteral formulation, comprising adding 1 mL 50% Dextrose Injection, USP to the glucagon vial provided in the Glucagon Emergency Kit for Low Blood Sugar, mixing to obtain a clear solution composition of the present invention which contains about 1 mg/mL glucagon, about 4.9% lactose and about 50% dextrose at a pH of about 2.5 to 3.5.

In one aspect, the present invention provides a method to prepare a parenteral formulation, comprising adding 0.7 mL 70% Dextrose Injection, USP and 0.3 mL Bacteriostatic Water for Injection, USP to the glucagon vial provided in the GlucaGen® Hypokit, mixing to obtain a clear solution composition of the present invention which contains about 1 mg/mL glucagon, about 10% lactose, about 50% dextrose and 4.5 mg/mL benzyl alcohol (as a preservative) at a pH of about 2.0 to 3.5.

In another aspect, the present invention provides a method to prepare a parenteral formulation, comprising adding 0.7 mL 70% Dextrose Injection, USP and 0.3 mL Bacteriostatic Water for Injection, USP to the glucagon vial from the GlucaGen® Hypokit, mixing to obtain a clear solution composition of the present invention which contains about 1 mg/mL glucagon, about 10% lactose, about 50% dextrose and 4.5 mg/mL benzyl alcohol (as a preservative) at a pH of about 2.0 to 3.5.

Given the known compositions of the Commercially Available Injectable Drugs/Preparations, a mixing ratio can be readily calculated to obtain a glucagon composition of the present invention. Some of the Commercially Available Injectable Drugs/Preparations such as 50% Dextrose Injection, USP are rather inexpensive and this method of mixing these Commercially Available Injectable Drugs/Preparations provides a benefit of a lower cost to the patients to obtain a pump-able glucagon composition. Injecting a high concentration dextrose composition of the present invention would therefore be appropriate for treating hypoglycemia since dextrose (aka D-glucose) is exactly what is needed to counteract low blood glucose.

The parenteral formulation of the present invention can be administered as is (undiluted) or diluted prior to administration. Dilutions can be made using a 5% or 10% dextrose solution or another common injection diluent. The route of administration may include, but is not limited to, intravenous, subcutaneous and intramuscular injections. The injection device for administration may be a syringe with a needle or an insulin/bi-hormonal pump with an infusion set. The injection speed may be rapid or slow. The parenteral formulation of the present invention can be provided in a vial, in a prefilled syringe or in a cartridge that is designed to fit inside an insulin/bi-hormonal pump. The dose can range from 0.001 mg to 3 mg glucagon depending upon the patient's condition and severity of hypoglycermia. Certain algorithms may be used with the bi-hormonal pump to control the injection volume and rate for the glucagon composition of the present invention, depending upon the insulin dosed, patient condition and severity of hypoglycermia.

In one aspect, a composition of this invention may be administered by a glucagon-only pump for treating conditions of acute or chronic metabolic diseases including, but not limited to, nocturnal hypoglycemia and hyperinsulinemia, respectively.

In one aspect, the composition of this invention remains gel-free after exposure to body temperature for 3.5 to 7 days.

In one aspect, the composition of this invention remains gel-free and is capable of passing the USP test specification for "PARTICULATE MATTER IN INJECTIONS" as described in the USP monograph <788> after exposure to body temperature for 3.5 to 7 days.

In one aspect, the composition of this invention retains no less than 65% of its initial glucagon concentration after storage at body temperature for 3.5 to 7 days. The 65% acceptance limit is defined by the United States Pharmacopeia Glucagon for Injection Monograph (USP-NF 36).

In another aspect, the composition of this invention retains no less than 65% of its initial glucagon concentration, remains gel-free and is capable of passing the USP test specification for "PARTICULATE MATTER IN INJECTIONS" as described in the USP monograph <788> after exposure at body temperature for 3.5 to 7 days while inside an insulin/bi-hormonal pump.

In one aspect, composition of this invention has a viscosity of no more than 50,000 mPas at room temperature.

In one aspect, composition of this invention is pump-able.

In one aspect, the composition of this invention is ready-to-use.

In one aspect, the composition of this invention is able to elevate blood glucose level to more than 100 mg/dl within 30 minutes following a subcutaneous injection.

In one aspect, the composition of this invention is filterable through a 0.2 or 0.45-micron membrane.

The present invention will be further understood by reference to the following non-limiting examples.

Example 1

The aim of this study was to determine the effect of high sugar concentrations (>10% w/v) on glucagon gelation. For each test composition, a lyo cake containing 1 mg glucagon and 100 mg lactose was prepared to have the same lyo cake composition as in the GlucaGen® Hypokit, except that the glucagon in these lyo cakes was produced synthetically rather than being produced by a recombinant DNA process. Each lyo cake was dissolved in about 1 mL of a sugar solution to obtain the final liquid compositions as shown in Table 1. For comparison, F12 was prepared to have the same composition as the final solution produced by mixing the 2 vials provided in the GlucaGen® Hypokit.

Each solution was filled into an insulin pump reservoir cartridge (Medtronic, Inc. Paradigm Reservoir # MMT-332A), placed on a shaker platform in a 37° C. incubator and subjected to constant agitation at 100 RPM. After 0, 3.5 and 7 days, a portion of the solution was removed and tested for presence of gelation using the USP<788>test method for Particulate Matter and for glucagon chemical stability using a RP-HPLC method for glucagon concentration and purity.

TABLE 1

| | Composition (% w/w) | | | | | | | | | | | | | | |
|---|---|---|---|---|---|---|---|---|---|---|---|---|---|---|---|
| | Formulation code | | | | | | | | | | | | | | |
| | F12 | F49 | F50 | F51 | F52 | F53 | F54 | F55 | F56 | F57 | F58 | F59 | F60 | F61 | F62 |
| Synthetic glucagon | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Lactose | 10 | 20 | 20 | 20 | 10 | 10 | 10 | 10 | 10 | 10 | 10 | 10 | 10 | 10 | 10 |
| Sucrose | | | | | 10 | 20 | 40 | | | | | | | | |
| Mannitol | | | | | | | | 10 | 20 | 25 | | | | | |
| Dextrose | | | | | | | | | | | 10 | 20 | 40 | 40 | 40 |
| Water | 89.9 | 79.9 | 79.9 | 79.9 | 79.9 | 69.9 | 49.9 | 79.9 | 69.9 | 64.9 | 79.9 | 69.9 | 49.9 | 49.9 | 49.9 |
| pH (Initial) | 2.7 | 2.4 | 2.7 | 3.0 | 2.7 | 2.7 | 2.7 | 2.7 | 2.7 | 2.7 | 2.7 | 2.7 | 2.7 | 2.4 | 3.0 |
| Total sugar (% w/v) | 10 | 20 | 20 | 20 | 20 | 30 | 50 | 20 | 30 | 35 | 20 | 30 | 50 | 50 | 50 |
| | Test Results | | | | | | | | | | | | | | |
| USP<788> Test (after 3.5 days at 37° C.) | Fail | Pass | Pass | Pass | Pass | Pass | Pass | Pass | Pass | Pass | Pass | Pass | Pass | Pass | Pass |
| USP<788> Test (after 7 days at 37° C.) | Fail | Pass | Pass | Fail | Pass | Pass | Pass | Fail | Pass | Pass | Pass | Pass | Pass | Pass | Pass |
| Glucagon recovery (% over the Initial Value) (after 3.5 days at 37° C./agitation) | 66.8 | 83.0 | 84.3 | 86.8 | 85.8 | 85.5 | 86.9 | 83.3 | 85.9 | / | 85.6 | 86.2 | 86.0 | 86.9 | 87.3 |
| Glucagon recovery (% over the Initial Value) (after 7 days at 37° C./agitation) | 30.1 | 75.6 | 81.1 | / | 84.1 | 82.4 | 83.5 | 82.1 | 64.5 | 71.4 | 82.7 | 78.6 | 85.0 | 84.2 | 72.6 |

These results reveal that a high concentration (≥20% w/v) of a sugar or a combination of sugars significantly improved glucagon solution stability at body temperature by inhibiting glucagon gelation and chemical degradation. By satisfying the ≥65% of initial glucagon concentration acceptance limit (Glucagon for Injection Monograph (USP-NF 36) after 3.5 or 7 days under simulated stress, the F49-F62 glucagon compositions demonstrate they have sufficient stability to allow semi-weekly or weekly replenishment in an insulin/bi-hormonal pump. In contrast, the reduced physical and chemical stability shown for the GlucaGen® Hypokit (F12) composition reveals that such replenishment intervals are not feasible.

Example 2

The aim of this study was to compare glucagon gelation and chemical degradation rates in solutions prepared by dissolving the lyo cake from the GlucaGen® Hypokit (Novo Nordisk) with either the kit's provided diluent (water) or with a concentrated sugar solution (40% dextrose). These reconstituted solutions were tested using the same procedures as in Example 1. The final solution compositions and test results are shown in Table 2. The glucagon in the GlucaGen® Hypokit lyo cake is manufactured using a recombinant DNA process.

TABLE 2

| | Starting Materials | |
|---|---|---|
| Lyo cake | Lyo cake (from the GlucaGen ® Hypokit) | |
| Diluent | Water (from the GlucaGen ® Hypokit) | A solution containing 40% w/w (or about 48% w/v) dextrose |
| | Concentration After Reconstitution | |
| Glucagon in the final solution | 0.1% w/v (or 1 mg/mL) glucagon hydrochloride | 0.1% w/v (or 1 mg/mL) glucagon hydrochloride |
| Lactose in the final solution | About 10% w/v | About 10% w/v |
| Dextrose in the final solution | 0 | About 48% w/v |
| Water in the final solution | About 89.9% w/v | About 42% w/v |
| Total sugar in the final solution | About 10% w/v | About 58% w/v |
| pH in the final solution | 2.9 | 2.7 |
| | Test Results | |
| Appearance after 3.5 days at 37° C. | An immobile, jelly-like clear gel that does not flow after inverting the container | Clear, colorless solution. No gel |
| Glucagon recovery (% over Initial Value) After 3.5 days at 37° C./agitation | 82.1 | 86.6 |
| Glucagon recovery (% over Initial Value) After 7 days at 37° C./agitation | 37.6 | 79.6 |

This study results indicate that a high concentration (≥20%) of a sugar or a sugar combination significantly improved glucagon stability at body temperature by inhibiting the gelation and chemical degradation in a solution containing the recombinant DNA-produced glucagon from the GlucaGen® Hypokit.

Example 3

The aim of this study was to compare glucagon chemical degradation rates between solutions prepared by dissolving the lyo cake from a commercially available glucagon kit with the kit's diluent (acidic water) or with a concentrated sugar solution (50% dextrose). Lyo cakes from the Glucagon for Injection (rDNA Origin) Kit from Eli Lilly and Company ("Glucagon Emergency Kit for Low Blood Sugar") were tested using the same procedure as in Example 1. The final solution compositions and test results are shown in Table 3. The glucagon in the Glucagon Emergency Kit for Low Blood Sugar lyo cake is manufactured using a recombinant DNA process.

TABLE 3

| | Starting Materials | | |
|---|---|---|---|
| Lyo cake | Lyo cake (from the Glucagon Emergency Kit for Low Blood Sugar) | | |
| Diluents | Acidic water (from the Glucagon Emergency Kit for Low Blood Sugar) | 40% (w/w) or about 47% w/v dextrose, pH 3.4 | Dextrose Monohydrate 50% Injection (Vetone), eqiv. to 45% w/v dextrose, 2523 mOsmol/liter |
| | Concentration After Reconstitution | | |
| Glucagon in the final solution | 0.1% (or 1 mg/mL) | 0.1% (or 1 mg/mL) | 0.1% (or 1 mg/mL) |
| Lactose in the final solution | About 4.9% w/v | About 4.9% w/v | About 4.9% w/v |
| Dextrose in the final solution | 0 | About 47% w/v | About 45% w/v |
| Water in the final solution | About 89.9% w/v | About 48% w/v | About 50% w/v |
| Total sugar in the final solution | About 10% w/v | About 51.9% w/v | About 49.9% w/v |
| pH in the final solution | 1.94 | 2.78 | 2.87 |
| | Test Results | | |
| Glucagon recovery (% over the Initial Value) After 14 days at 37° C./agitation | 49.7 | 72.0 | 70.6 |
| Glucagon chromatographic purity (% glucagon peak area over total peak area) After 14 days at 37° C./agitation | 59.4 | 78.9 | 78.6 |

These results indicate that a high concentration (≥20%) of a sugar or a sugar combination significantly improved glucagon solution stability at body temperature by inhibiting the chemical degradation.

Example 4

The aim of this study was to compare glucagon gelation and chemical degradation rates in solutions containing various sugars, antioxidants and preservatives. The lyo cakes were prepared to have the same lyo cake composition of GlucaGen® Hypokit, except that the glucagon in these lyo cakes was produced synthetically rather than being produced by a recombinant DNA process. The stability tests followed the same procedure as in Example 1. The final solution compositions and test results are shown in Table 4.

TABLE 4

| Composition (% w/v) | | | | | | | | | | | |
|---|---|---|---|---|---|---|---|---|---|---|---|
| Synthetic glucagon | 0.1 | 0.1 | 0.1 | 0.1 | 0.1 | 0.1 | 0.1 | 0.1 | 0.1 | 0.1 | 0.1 |
| Lactose | 10 | 10 | 10 | 10 | 10 | 10 | 10 | 10 | 10 | 10 | 10 |
| Dextrose | | 50 | 50 | 50 | 50 | 70 | 70 | 70 | | | |
| Mannitol | | | | | | | | | 20 | 20 | 20 |
| EDTA disodium dehydrate | | | 0.005 | | | | 0.005 | | | | |
| EDTA Calcium, disodium | | | | 0.006 | | | | | | 0.006 | |
| m-cresol | | | | | 0.315 | | | 0.315 | | | 0.315 |
| Total sugar in the final solution (w/v %) | 10 | 60 | 60 | 60 | 60 | 80 | 80 | 80 | 30 | 30 | 30 |
| pH in the final solution | 2.7 | 2.7 | 2.7 | 2.7 | 2.7 | 2.7 | 2.7 | 2.7 | 2.7 | 2.7 | 2.7 |
| Test Results | | | | | | | | | | | |
| USP<788> Test (after 3.5 days at 37° C.) | Fail | Pass | Pass | Pass | Pass | Pass | Pass | Pass | Pass | Pass | Pass |
| USP<788> Test (after 7 days at 37° C.) | Fail | Pass | Pass | Fail | Fail | Pass | Pass | Pass | Pass | Fail | Fail |
| Glucagon recovery (% over Initial Value) (after 3.5 days at 37° C./agitation) | 72.3 | 88.5 | 86.9 | 87.7 | 86.9 | 85.0 | 90.7 | 3.2 | 68.4 | 72.5 | 62.2 |
| Glucagon recovery (% over Initial Value) (after 7 days at 37° C./agitation) | 16.5 | 82.2 | 77.2 | 77.2 | 76.5 | 82.4 | 86.8 | 25.0 | 8.5 | 38.3 | 56.3 |

These results indicate that high concentrations (≥20%) of a sugar or a sugar combination significantly improved glucagon stability at body temperature (as determined by both reduced gelation and chemical degradation of the synthetic glucagon) compared to a composition containing less than 20% sugar. An antioxidant (e.g. EDTA) and preservative (e.g. cresol) may be included in the inventive compositions.

Example 5

The aim of this study was to demonstrate safety and tolerability of a high concentration sugar solution following subcutaneous injection using an insulin pump. A commercially available injectable preparation (USP Normal Saline (Nurse Assist, Inc.)) or a 50% Dextrose Injection, USP (Hospira) was filled into the pump reservoir of a MiniMed Paradigm (Medtronic, Inc.) insulin pump and loaded into the pump. An infusion set (Quick-set Paradigm (Medtronic, Inc.) was attached to the pump. The infusion set tubing was primed with the liquid before the indwelling catheter was inserted into the abdominal skin of a human volunteer (this inventor Andrew Chen). Minibolus injections of 10, 20, 30 or 50 µL were repeatedly administered for both Normal Saline and 50% Dextrose Injection, USP. For both injected fluids, the subject did not report any pain, discomfort or any sensation during or after the injections. No edema, erythema or any abnormality was observed at the injection site after the indwelling catheter was removed. This finding thus demonstrated that a high sugar solution (e.g., 50% Dextrose Injection) is safe to inject subcutaneously. This finding was unexpected and contradictory to the conventionally held belief that such hypertonic dextrose solutions would cause pain at the injection site due to their high osmolarity. Furthermore, this finding supports the safety of subcutaneous or intramuscular injections of hypertonic sugar solutions such as the glucagon composition of the present invention.

Modifications and variations of the present invention will be obvious to those skilled in the art from the foregoing detailed description and are intended to fall within the scope of the following claims. The teachings of all references cited herein are specifically incorporated by reference.

What is claimed is:

1. A parenteral, hypertonic solution composition, comprising:
   a) glucagon at a concentration of 0.01 mg/mL to 3 mg/mL;
   b) a sugar at a concentration of no less than 20% w/v to about 80% w/v, wherein the sugar is a mixture of lactose and dextrose with the concentration of lactose up to about 21.6% w/v, and the sugar to glucagon weight ratio is between 6.67:1 to 8000:1; and
   c) water, wherein the pH is between about 1.5 to about 7, wherein the composition is an aqueous composition having an osmotic pressure exceeding 600 mOsmol/L and is substantially free of an organic solvent.

2. The composition of claim 1, wherein 0.5 mg/mL to 2 mg/mL glucagon is present in the composition.

3. The composition of claim 1, wherein about 1 mg/mL glucagon is present in the composition.

4. The composition of claim 1, wherein the glucagon is synthetically produced using a recombinant DNA process obtained from an animal source or a combination thereof.

5. The composition of claim 1, wherein the glucagon is a hydrochloride salt.

6. The composition of claim 1, wherein the pH of the composition is between 1.5 and 3.5.

7. The composition of claim 1, wherein an acid is present in the composition.

8. The composition of claim 7, wherein an acid is selected from: acetic acid, hydrochloric acid, methanesulfonic acid, phosphoric acid, succinic acid, sulfuric acid, tartaric acid, and a combination thereof.

9. The composition of claim 1, wherein a preservative is present in the composition.

10. The composition of claim 9, wherein the preservative is selected from: cresols, phenol, benzyl alcohol, ethanol, chlorobutanol, parabens, imidura, benzylkonium chloride, EDTA or its salt, or a combination thereof.

11. The composition of claim 1, comprising:
a) glucagon at about 1 mg/mL;
b) a sugar which is a mixture of lactose and, dextrose having a concentration of 50% w/v to about 80% w/v;
c) water; and
d) hydrochloric acid
wherein the composition has a pH between 1.5 and 3.5.

12. The composition of claim 1, comprising:
a) glucagon at about 1 mg/mL;
b) dextrose at a concentration of no less than 20 to about 80% w/v;
c) water at about 20 to 80% w/v; and
d) hydrochloric acid
wherein the composition has a pH between 1.5 and 3.5.

13. The composition of claim 1, comprising:
a) glucagon at about 1 mg/mL;
b) lactose at a concentration of about 4.9% w/v to 10% w/v;
and dextrose at a concentration of about 45% w/v to about 70% w/v;
c) water; and
d) hydrochloric acid
wherein the composition has a pH between 1.5 and 3.5.

14. The composition of claim 1, wherein the glucagon is from a lyophilized cake and sugar is provided by a Commercially Available Injectable Drug/Preparation.

15. The composition of claim 14, wherein the dextrose is selected from 10% Dextrose Injection USP, 50% Dextrose Injection USP, 70% Dextrose Injection USP, or a combination thereof.

16. The composition of claim 1, wherein the composition was formed by dissolving the glucagon and the sugar from the same lyophilized cake.

17. The composition according to claim 1, wherein said composition is administered to a human or animal subject by a subcutaneous, intramuscular or intravenous injection using a syringe, pen-injector, auto-injector, Uniject injector system, needleless or needle-free injector, infusion pump, insulin pump, bi-hormonal pump, or other injection device.

18. A kit comprising a container comprising dry glucagon and another container comprising a solution comprising dextrose at a concentration of 20% w/v or more; or a kit comprising a container comprising dry glucagon and a dry dextrose and another container comprising water, where mixing the contents in the two containers forms a solution as claimed in claim 1.

19. A method for preparing a composition of claim 1, comprising dissolving:
a) glucagon to a final concentration of about 0.1 to 0.3 mg/mL; and
b) a sugar to a final concentration of no less than a bout 20% w/v in water to form a clear solution.

20. A method of treatment or prophylaxis for diabetes, hypoglycemia, hyperinsulinemia or other medical disorders using glucagon, or for reducing intestinal motility during radiologic examination of the stomach, duodenum, small bowel, and colon when diminished intestinal motility in a human or animal subject, said method comprising administering to said subject an effective amount of a solution as claimed in claim 1.

21. A method of treatment of prophylaxis for a patient that has hypoglycemia, the method comprising administering into the soft tissue of the patient a composition of claim 1.

* * * * *